US006793677B2

(12) United States Patent
Ferree

(10) Patent No.: US 6,793,677 B2
(45) Date of Patent: *Sep. 21, 2004

(54) METHOD OF PROVIDING CELLS AND OTHER BIOLOGIC MATERIALS FOR TRANSPLANTATION

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

This patent is subject to a terminal disclaimer.

(21) Appl. No.: 10/143,275

(22) Filed: May 10, 2002

(65) Prior Publication Data

US 2002/0128718 A1 Sep. 12, 2002

Related U.S. Application Data

(63) Continuation-in-part of application No. 09/688,716, filed on Oct. 16, 2000, now Pat. No. 6,454,804, which is a continuation-in-part of application No. 09/639,309, filed on Aug. 14, 2000, now Pat. No. 6,419,702, which is a continuation-in-part of application No. 09/638,726, filed on Aug. 14, 2000, now Pat. No. 6,340,369.
(60) Provisional application No. 60/148,913, filed on Aug. 13, 1999.

(51) Int. Cl.[7] .................................................. A61F 2/44
(52) U.S. Cl. ..................... 623/17.11; 623/908; 427/93.7
(58) Field of Search .......................... 623/17.11–17.16; 424/93.7, 423; 62/78; 435/395

(56) References Cited

U.S. PATENT DOCUMENTS

| | | | | |
|---|---|---|---|---|
| 2,677,369 A | | 5/1954 | Knowles ....................... 128/92 |
| 3,366,975 A | | 2/1968 | Pangman ......................... 3/36 |
| 3,426,364 A | | 2/1969 | Lumb ............................... 3/1 |
| 3,551,560 A | | 12/1970 | Thiele .......................... 424/95 |
| 3,593,342 A | | 7/1971 | Niebauer ........................... 3/1 |
| 3,648,294 A | | 3/1972 | Shahrestani ....................... 3/1 |
| 3,855,638 A | | 12/1974 | Pilliar ............................. 3/1 |
| 3,867,728 A | | 2/1975 | Stubstad et al. ................... 3/1 |
| 3,875,595 A | | 4/1975 | Froning ............................ 3/1 |
| 3,883,902 A | | 5/1975 | Lynch ............................ 3/36 |
| 3,918,099 A | * | 11/1975 | Fuhr et al. ................ 623/23.71 |
| 4,229,839 A | | 10/1980 | Schwemmer ................... 1/1.91 |
| 4,309,777 A | | 1/1982 | Patil ............................ 3/1.91 |
| 4,349,921 A | | 9/1982 | Kuntz ............................. 3/1 |
| 4,353,888 A | * | 10/1982 | Sefton ........................ 424/424 |
| 4,663,358 A | | 5/1987 | Hyon et al. .................... 521/64 |
| 4,673,649 A | * | 6/1987 | Boyce et al. ................. 435/378 |
| 4,707,872 A | | 11/1987 | Hessel ........................... 5/451 |
| 4,714,469 A | | 12/1987 | Kenna .......................... 623/17 |
| 4,759,766 A | | 7/1988 | Buettner-Janz et al. ........ 623/17 |
| 4,772,287 A | | 9/1988 | Ray et al. ...................... 623/17 |
| 4,801,299 A | | 1/1989 | Brendel et al. ............. 623/16.11 |
| 4,863,477 A | | 9/1989 | Monson ......................... 623/17 |
| 4,874,389 A | | 10/1989 | Downey ........................ 623/17 |
| 4,904,260 A | | 2/1990 | Ray et al. ...................... 623/17 |
| 4,911,718 A | | 3/1990 | Lee et al. ...................... 623/17 |
| 4,917,704 A | | 4/1990 | Frey et al. ..................... 623/17 |
| 4,932,969 A | | 6/1990 | Frey et al. ..................... 623/17 |
| 4,946,378 A | | 8/1990 | Hirayama et al. ............. 623/17 |
| 5,002,576 A | | 3/1991 | Fuhrmann et al. ............. 623/17 |
| 5,035,716 A | | 7/1991 | Downey ........................ 623/17 |
| 5,047,055 A | | 9/1991 | Bao et al. ...................... 623/17 |
| 5,071,437 A | | 12/1991 | Steffee .......................... 623/17 |
| 5,108,438 A | | 4/1992 | Stone ........................... 623/17 |
| 5,123,926 A | | 6/1992 | Pisharodi ...................... 623/17 |
| 5,131,850 A | * | 7/1992 | Brockbank ................... 435/1.3 |
| 5,171,280 A | | 12/1992 | Baumgartner ................. 623/17 |
| 5,171,281 A | | 12/1992 | Parsons et al. ................ 623/17 |
| 5,192,326 A | | 3/1993 | Bao et al. ...................... 623/17 |
| 5,246,458 A | | 9/1993 | Graham ........................ 623/17 |
| 5,258,031 A | | 11/1993 | Salib et al. .................... 623/17 |
| 5,258,043 A | | 11/1993 | Stone ........................... 623/66 |
| 5,314,477 A | | 5/1994 | Marnay ......................... 623/17 |
| 5,320,644 A | | 6/1994 | Baumgartner ................. 623/17 |
| 5,370,697 A | | 12/1994 | Baumgartner ................. 623/17 |
| 5,375,823 A | | 12/1994 | Navas .......................... 267/195 |
| 5,401,269 A | | 3/1995 | Buttner-Janz et al. ......... 623/17 |
| 5,425,773 A | | 6/1995 | Boyd et al. .................... 623/17 |
| 5,458,642 A | | 10/1995 | Beer et al. ..................... 623/17 |

(List continued on next page.)

OTHER PUBLICATIONS

Choi, W Sung et al., Distinct Responses of Annulus Fibrosis and Nucleus Pulposus Cells to Growth Factors, 47th Annual Meeting, Orthopaedic Research Society, Feb. 25–28, 2001, San Francisco, California..*
Lumbar Intervertebral Disc Transfer a Canine Study, Steven Frick MD, SPINE vol. 19 No. 16 pp. 1826–1835, 1994.
Orthopedics Today, Jul. 2000.
"Proceedings 14th Annual Meeting" North American Spine Society, Oct. 1999.
"Proceedings 13th annual Meeting" North American Spine Society, Oct. 1998.
North American Spine Society 13 Annual Meeting San Francisco Hilton and towers Oct. 28–31, 1998; Baron Lonner Md et al. Tissue Enineered Regeneration of the Intervertebral Disc.

*Primary Examiner*—Suzette J. Jackson
(74) *Attorney, Agent, or Firm*—Gifford, Krass, Groh, Sprinkle, Anderson & Citkowski, PC

(57) ABSTRACT

Tissue culture and banking is used to guard against the spread of transmittable diseases. In one disclosed example, living nucleus pulposis cells obtained from recently deceased human or animal donors are used to restore disc function and eliminate pain in patients with disc disease. In the preferred embodiment, the donor nucleus is morselized to allow insertion through a small puncture in the annulus fibrosis with a needle and syringe. Although the description makes specific reference to human disc cells, the invention may be used as a way to provide disease-free disc tissue derived from animal sources, and is applicable as well to other types of biologic tissues and materials such pancreas cells, cartilage cells, and so forth. Additional therapeutic substances like culture medium, growth factors, differentiation factors, hydrogels polymers, antibiotics, anti-inflammatory medications, or immunosuppressive medications could be added to the transplanted cells or tissue.

3 Claims, No Drawings

U.S. PATENT DOCUMENTS

| | | | |
|---|---|---|---|
| 5,464,439 A | 11/1995 | Gendler | 623/16.11 |
| 5,514,180 A | 5/1996 | Heggeness et al. | 623/17.11 |
| 5,534,028 A | 7/1996 | Bao et al. | 623/17 |
| 5,534,030 A | 7/1996 | Navarro et al. | 623/17 |
| 5,545,229 A | 8/1996 | Parsons et al. | 623/17 |
| 5,571,083 A * | 11/1996 | Lemelson | 604/522 |
| 5,782,851 A * | 7/1998 | Rassman | 606/167 |
| 5,882,328 A * | 3/1999 | Levy et al. | 604/20 |
| 5,964,096 A * | 10/1999 | Watson et al. | 62/78 |
| 6,110,482 A * | 8/2000 | Khouri et al. | 424/423 |
| 6,184,033 B1 * | 2/2001 | Smikodub | 435/366 |
| 6,197,586 B1 * | 3/2001 | Bhatnagar et al. | 435/395 |
| 6,340,369 B1 * | 1/2002 | Ferree | 623/17.11 |
| 6,419,702 B1 * | 7/2002 | Ferree | 623/17.11 |
| 6,454,804 B1 * | 9/2002 | Ferree | 623/17.11 |
| 6,455,311 B1 * | 9/2002 | Vacanti | 435/395 |
| 6,489,165 B2 * | 12/2002 | Bhatnagar et al. | 435/395 |
| 6,541,028 B1 * | 4/2003 | Kuri-Harcuch et al. | 424/443 |
| 2001/0006948 A1 * | 7/2001 | Kang et al. | 514/44 |
| 2002/0115208 A1 * | 8/2002 | Mitchell et al. | 435/325 |
| 2003/0125782 A1 * | 7/2003 | Streeter | 607/88 |

* cited by examiner

METHOD OF PROVIDING CELLS AND OTHER BIOLOGIC MATERIALS FOR TRANSPLANTATION

REFERENCE TO RELATED APPLICATIONS

This application is a continuation-in-part of U.S. patent application Ser. No. 09/639,309, filed Aug. 14, 2000 now U.S. Pat. No. 6,419,702, which claims priority of U.S. Provisional Patent Application Serial No. 60/148,913, filed Aug. 13, 1999; and is a continuation-in-part of U.S. patent application Ser. No. 09/688,716, filed Oct. 16, 2000 now U.S. Pat. No. 6,454,804, which is a continuation-in-part of U.S. patent application Ser. No. 09/638,726, filed Aug. 14, 2000, now U.S. Pat. No. 6,340,369. The entire content of each application is incorporated herein by reference.

FIELD OF THE INVENTION

This invention relates generally to the treatment of diseased or traumatized intervertebral discs, and more particularly, to transplantation of the nucleus pulposis in conjunction with such treatment.

BACKGROUND OF THE INVENTION

Intervertebral discs provide mobility and a cushion between the vertebrae. At the center of each disc is the nucleus pulposus which, in the adult human, is composed of cells and an insoluble extracellular matrix which is produced by the nucleus itself. The extracellular matrix is composed of collagen, proteoglycans, water, and noncollagenous proteins. The nucleus pulposus is surrounded by the annulus fibrosis, which is composed of cells (fibrocyte-like and chondrocyte-like), collagen fibers, and non-fibrillar extracellular matrix. The components of the annulus are arranged in 15–25 lamellae around the nucleus pulposus.

The cells of the nucleus pulposus have chondrocyte-like features. In an adult human, the cells of the nucleus pulposis obtain nutrients and eliminate waste by diffusion through blood vessels in the endplates of the vertebrae adjacent to the disc. Blood vessels do not course into the nucleus pulposis. The relative vascular isolation of the nucleus pulposis imparts isolation of nucleus pulposis cells from the body's immune system.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof. My pending U.S. patent application Ser. No. 09/415,382 discloses disc replacement methods and apparatus using synthetic materials.

Unfortunately, disc replacement using synthetic materials does not restore normal disc shape, physiology, or mechanical properties. Synthetic disc replacements tend to wear out, resulting in premature failure. The problems associated with the wear of prosthetic hip and knees are well known to those skilled in orthopedic surgery. The future of treating degenerative disc disease therefore lies in treatments which preserve disc function. If disc function could be restored with biologic replacement or augmentation, the risk of premature wearout would be minimized, if not eliminated.

My U.S. patent application Ser. No. 09/639,309, filed Aug. 14, 2000, is directed to a method of treating a diseased or traumatized intervertebral disc through the transplantation of nucleus pulposis cells. Broadly according to the method, live nucleus pulposis cells are harvested from a human or animal donor and introduced into the disc being treated. The harvested nucleus pulposus cells are preferably kept viable until placed into the disc being treated.

A preferred embodiment includes morselizing the harvested nucleus pulposus cells and extracellular matrix, forming a passageway through the annulus fibrosis, and transplanting the harvested nucleus pulposus cells and extracellular matrix into the disc through the passageway. For example, the harvested nucleus pulposus cells and extracellular matrix may be introduced into the disc using a needle and syringe or small cannula.

One or more therapeutic substances may be added to the harvested nucleus pulposus cells and extracellular matrix including culture media, growth factors, differentiation factors, hydrogels, polymers, antibiotics, anti-inflammatory medications, or immunosuppressive medications. Alternatively the step of transplanting the harvested nucleus pulposus cells and extracellular matrix may include percutaneously or laparoscopically injecting the engineered disc tissue into the disc being treated.

The relative vascular isolation of the nucleus pulposis imparts isolation of nucleus pulposis cells from the body's immune system. However, even with the lack of an immune system response, the transplantation risks viral disease transmission, i.e. hepatitis, HIV etc. The risk of disease transmission increases in direct proportion to the number donors who provide disc tissue.

SUMMARY OF THE INVENTION

Broadly, this invention resides in tissue banking to guard against the spread of transmittable diseases. Although the description makes specific reference to human disc cells, the invention may be used as a way to provide disease-free disc tissue derived from animal sources, and is applicable as well to other types of biologic tissues and materials such pancreas cells, cartilage cells, and so forth.

DETAILED DESCRIPTION OF THE INVENTION

Tissue donation from a live donor allows close monitoring of the donor for months or years. According to the invention, such monitoring would include testing the donor for transmittable diseases. Using this invention tissue banks could carry live cells derived from a single donor for an extended time, for example, for years. Thus, surgeons would have access to unlimited, known healthy, cells, tissues and other biologic materials for transplantation purposes.

Cell lines obtained from recently deceased humans would be tested for transmittable diseases. Furthermore, careful study of patient's receiving the cell transplant, from a deceased donor, would allow the elimination of cell lines that are discovered to carry transmittable disease. The invention further allows tissue banks to select cell lines that demonstrate desirable features, for example, cells that demonstrate longevity or low risk of immune reaction.

According to another aspect of the invention, the cells would be treated to reduce immunogenicity. For example, the cells could be cyropreserved. Future developments in genetic engineering may also allow the manipulation of cells to reduce their immunogenicity. Cells from a recently deceased or a live tissue donor would be cloned and grown in tissue culture. Although human cells are preferred, the invention could be used as a way to provide disease-free biologic material derived from animal sources.

Depending upon the extent of the harvest, the recipient may function at least in part as a donor, or the tissues from others, including fetal or embryo, such as stem cells, sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described in the literature.

Similarly, the guidelines for storage of living tissues are well known to those skilled in the art. The text "Organ Preservation for Transplantation" by Karow and Pego, 1981, describes such methods. Briefly, the tissue storage method must maintain cell viability and preserve sterility. Examples of present storage methods include: refrigeration, refrigeration with tissue culture medium such as: hemolyzed serum, autologous serum, Medium 199 with 5% dextran (McCarey-Kaufman medium), Medium 199 with chondroitin sulfate, Medium 199 supplemented with inorganic salts, short chain fatty acids, and/or ketone bodies, and cryopreservation techniques, among others. Details are provided in U.S. Pat. Nos. 4,695,536 and 4,873,186, the entire contents of which are incorporated herein by reference.

In addition to the primary cells or other biologic materials, therapeutic substances could be added including, for example, resorbable culture medium, tissue growth or differentiation factors (recombinant generated morphogenetic proteins, PDGF, TGF-$\beta$, EGF/TGF-$\alpha$, IGF-I, $\beta$FGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc.

Thus, according to the invention, surgeons would have access to unlimited, known healthy, cells and other biologic material, including disc tissue for transplantation purposes. Furthermore, careful study of patients receiving the cell transplant from a deceased donor would allow the elimination of cell lines that are discovered to carry transmittable disease.

I claim:

1. A method of transplanting cells or other biologic materials, comprising the steps of:

harvesting nucleus pulposus cells or tissue from a live human or animal donor;

culturing and banking the cells or tissue to ensure that they are free from communicable diseases;

morselizing the harvested nucleus pulposus tissue;

forming a passageway through the annulus fibrosis; and transplanting the harvested nucleus pulposus cells into the disc through the passageway.

2. The method of claim 1, further including the step of adding one or more therapeutic substances to the harvested cells or tissue.

3. The method of claim 2, wherein the therapeutic substances include one or more of the following:

culture media, growth factors, differentiation factors, hydrogels, polymers, antibiotics, anti-inflammatory medications, or immunosuppressive medications.

* * * * *